United States Patent [19]

Hughes et al.

[11] 4,062,815

[45] Dec. 13, 1977

[54] RESIN PEPTIDES

[75] Inventors: John Lawrence Hughes, Kankakee; Jay Kenneth Seyler, Bourbonnais; Robert Chung-Huang Liu, Kankakee, all of Ill.

[73] Assignee: Armour Pharmaceutical Company, Phoenix, Ariz.

[21] Appl. No.: 615,303

[22] Filed: Sept. 22, 1975

Related U.S. Application Data

[62] Division of Ser. No. 496,539, Aug. 12, 1974, Pat. No. 3,926,938.

[51] Int. Cl.$^2$ .................... C07C 103/52; C08L 89/00
[52] U.S. Cl. ................................ 260/8; 260/112.5 R; 260/112.5 T; 424/177
[58] Field of Search .............. 260/112.5 R, 8, 112.5 T

[56] References Cited

U.S. PATENT DOCUMENTS 3,891,614   6/1975   Sakakibara et al. .......... 260/112.5 T

OTHER PUBLICATIONS

Izumiya et al.: Japan, Kokai 74–80087 (8-2-74); cited from CA 82:86642p.
J. M. Stewart and J. D. Young, "Solid Phase Peptide Synthesis," Freeman and Co., San Francisco, 1969, pp. 13-19, 22, 23.

*Primary Examiner*—Dolph H. Torrence
*Attorney, Agent, or Firm*—Richard R. Mybeck; Frank T. Barber; Carl C. Batz

[57]           ABSTRACT

Resin peptides useful in the preparation of salmon calcitonin are disclosed along with processes for preparing the same. The invention also embraces peptides from which the resin moiety has been cleaved and which are useful in the synthesis of salmon calcitonin together with processes for preparing the cleaved peptides. In general, the processes involve the solid phase synthesis procedures.

2 Claims, No Drawings

RESIN PEPTIDES

This is a division of Application Ser. No. 496,539 filed Aug. 12, 1974, now U.S. Pat. No. 3,926,938.

The invention deals with new compounds containing an amino acid chain similar to that of salmon calcitonin and new methods for closing the ring structure in such compounds to produce calcitonin.

This invention relates to the hormone calcitonin and to substances having biological activity similar to calcitonin and to substances which may be converted into such biologically active substances. The invention deals also with processes for the preparation of these substances.

BACKGROUND

It is known that biological substances of natural origin can be obtained from the glands of land and aquatic animals and that such substances can be used to treat hormonal deficiencies in man and other animals. Among such substances is the hormone calcitonin. This hormone has been found to be particularly useful in the treatment of Paget's Disease (See the article by DeRose et al entitled "Treatment of Paget's Disease with Calcitonin" in *Seminars in Drug Treatment*, Vol. 2, No. 1.

Calcitonins have been obtained from bovine, porcine and human sources and these have been found to exhibit hormonal action when administered to animals or to man. The most active of the calcitonins has been obtained from salmon fishes. (Copp, D. H., Parkes, C. O., and O'Dor, R. K., Feder. Proc. 28/2, 413 [1969]). The calcitonin extract obtained from salmon has been purified (Keutmann, H. T., et al., J. Biol. Chem., 245, 1491–6 [1970]) and its structure elucidated (Niall, H. D., et. al., Proc. Nat. Acad. Sci 64, 771–8 [1969]). The material was found to be a 32 amino acid carboxyl terminal amide peptide containing a disulfide bridge between the cysteine moieties at positions 1 and 7. Using the abbreviatons CYS, SER, ASN, etc. to represent the amino acid residues, the formula for salmon calcitonin may be written as follows:

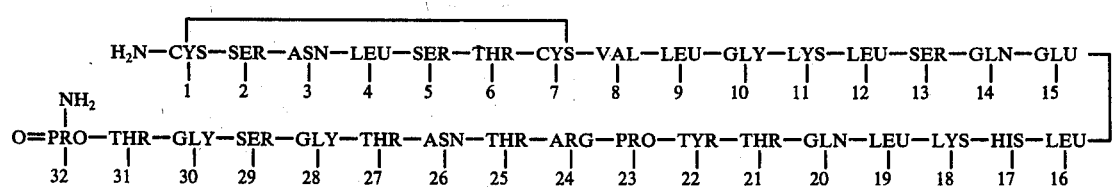

The burden of routinely collecting the small ultimobranchial gland of salmon from which calcitonin is obtained, the low yield of active extract obtained, and the small and rapidly diminishing size of the salmon catch, produce supply problems which cry out for a practical method for the synthesis of salmon calcitonin, or for the synthesis of substances not heretofore known which can be converted to substances having calcitonin hormonal activity. We have therefore set about to discover such methods and substances.

Although the synthesis of salmon calcitonin using classical peptide synthesis has been reported (Guttmann, S., et. al., Helv. Chim. Acta 52, 1789–1795 [1969], the art has been seeking processes which would be more practical for larger scale commercial production. Although methods are known for the synthesis of certain peptides by addition of amino acids singularly, (Merrifield, R. B., J. Am. Chem. Soc., 85, 2139–54 [1963], and Pietta, P. S. and Marshall, G. R., Chem. Commun., 650 [1970]) the synthesis of salmon calcitonin by such addition has not heretofore been reported.

DESCRIPTION OF INVENTION

In general we use a solid phase type of synthesis and start with a resin called benzhydryl amine resin (BHA resin). This resin is derived from a cross-linked polystyrene bead resin manufactured by copolymerization of styrene and divinylbenzene. Resin of this type is known and its preparation is further demonstrated by Pietta et al (Pietta, P. S. and Marshall, G. R., Chem. Commun., 650 [1970]). This cross-linked polystyrene BHA resin is available from chemical supply houses. We use the designation

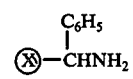

to represent the BHA resin in which $\text{X}$ is the polystyrene portion of the resin.

RESIN PEPTIDE SYNTHESIS

In this synthesis the amino acids are added one at a time to the insoluble resin until the total peptide sequence has been built up on the resin. The functional groups of the amino acids are protected by blocking groups. The α-amino group of the amino acids is protected by a tertiary butyloxycarbonyl group or an equivalent thereof. This α-teritiary butyloxycarbonyl group we designate as BOC. The hydroxyl functions of serine and threonine are protected by a benzyl or benzyl derivative group such as 4-methoxybenzyl, 4-methylbenzyl, 3,4-dimethyl benzyl, 4-chlorobenzyl, 2,6-dichlorobenzyl, 4-nitrobenzyl, benzhydryl or an equivalent thereof. We use the term BZ to represent benzyl or benzyl derivative group. The hydroxyl function of tyrosine may be unprotected, may be protected by a benzyl or benzyl derivative group as described above, as a BZ group, or may be protected by a benzyloxycarbonyl or a benzyloxycarbonyl derivative such as a 2-chlorobenzyloxycarbonyl or a 2-bromobenzyloxycarbonyl group or equivalent thereof. We use the term W to represent either no protective group, a BZ group, a benzyloxycarbonyl group or a benzyloxycarbonyl derivative group. The thiol function of cysteine may be protected by benzyl or benzyl derivative protective groups described above and designated BZ or by an n-alkylthio group such as methylthio, ethylthio, n-propylthio, n-butylthio or equivalents thereof. We use the character R to represent the n-alkylthio groups or the BZ groups on cysteine. The guanidino function of arginine may be protected by a nitro group, a tosyl group or an equivalent thereof. We use the character T to represent either a nitro group or a tosyl group. The ε-amino function of lysine may be protected by a benzyloxycarbonyl group or a benzyloxycarbonyl derivative such as 2-chlorobenzyloxycarbonyl, 2-bromobenzyloxycarbonyl, 3,4-dimethylbenzyloxycarbonyl or equivalents thereof. We use the character V to represent benzyloxy carbonyl group or a benzyloxycarbonyl derivative group. The protective groups used on the imidazole nitrogen of histidine are the benzyloxycarbonyl group and benzyloxycarbonyl derivatives such as described above for lysine and are designated as V. The γ-carboxylic acid group of glutamic acid is protected by a benzyl or benzyl derivative group such as described for the protection of the hydroxyl function of serine and threonine. These protective groups are represented by the character BZ.

As may be seen from the formula of salmon calcitonin above given, 32 amino acids are involved and in this formula the positions are numbered according to the accepted custom beginning at position 1 for the CYS on one end of the chain and ending with PRO at position 32 at the other end of the chain. For clarity of description this same numbering system will be followed in referring to the cycles of the synthesis. The assembly of the amino acids begins with cycle 32 which involves the coupling of proline and continues with cycle 31 which involves the coupling of threonine, etc.

Preferred amino acid reactants for use in each of the 32 cycles of the synthesis are given in the following Table I:

TABLE I

| Number | Amino Acid Reactant |
|---|---|
| 32 | BOC-L-proline |
| 31 | BOC-O-benzyl-L-threonine |
| 30 | BOC-glycine |
| 29 | BOC-O-benzyl-L-serine |
| 28 | BOC-glycine |
| 27 | BOC-O-benzyl-L-threonine |
| 26 | BOC-L-asparagine p-nitrophenyl ester |
| 25 | BOC-O-benzyl-L-threonine |
| 24 | BOC-Ω-nitro-L-arginine or BOC-Ω-tosyl-L-arginine |
| 23 | BOC-L-proline |
| 22 | BOC-O-benzyl-L-tyrosine, BOC-L-tyrosine, or BOC-O-2-bromobenzyloxycarbonyl-L-tyrosine |
| 21 | BOC-O-benzyl-L-threonine |
| 20 | BOC-L-glutamine p-nitrophenyl ester |
| 19 | BOC-L-leucine |
| 18 | BOC-ε-CBZ-L-lysine or BOC-ε-2-chlorobenzyloxycarbonyl-L-lysine |
| 17 | BOC-N(im)-CBZ-L-histidine |
| 16 | BOC-L-leucine |
| 15 | BOC-L-glutamic acid γ-benzyl ester |
| 14 | BOC-L-glutamine p-nitrophenyl ester |
| 13 | BOC-L-benzyl-L-serine |
| 12 | BOC-L-leucine |
| 11 | BOC-ε-CBZ-L-lysine or BOC-ε-2-chlorobenzyloxycarbonyl-L-lysine |
| 10 | BOC-glycine |
| 9 | BOC-L-leucine |
| 8 | BOC-L-valine |
| 7 | BOC-S-ethylthio-L-cysteine, BOC-S-methylthio-L-cysteine, BOC-S-n-propylthio-L-cysteine or BOC-S-n-butylthio-L-cysteine |
| 6 | BOC-O-benzyl-L-threonine |
| 5 | BOC-O-benzyl-L-serine |
| 4 | BOC-L-leucine |
| 3 | BOC-L-asparagine p-nitrophenyl ester |
| 2 | BOC-O-benzyl-L-serine |
| 1 | BOC-S-p-methoxybenzyl-L-cysteine, BOC-S-benzyl-L-cysteine or BOC-S-3,4-dimethylbenzyl-L-cysteine |

Each of the amino acid derivatives mentioned in Table I may be purchased from supply houses except perhaps the derivative mentioned for use in cycle No. 7. These materials useful in cycle 7 may be prepared according to the method described in the literature (U. Weber and P. Hartter, Hoppe-Seyler's, Z. Physiol. Chem. 351, 1384–8 [1970]).

CYCLE 32

Coupling of Proline to BHA Resin

The reaction vessel used in all steps of the resin peptide synthesis may be a glass vessel equipped with inlet ports at the top for addition of materials and a sintered glass disk at the bottom for removal of soluble reaction mixtures and wash solvents by filtration. Filtration can be performed either by vacuum or the use of nitrogen pressure. The contents of the vessel can be agitated by shaking the entire vessel or by a mechanical stirrer.

In cycle 32 the BHA resin is placed in the reaction vessel and suspended in a solvent such as methylene chloride, chloroform, dimethylformamide, benzene or equivalents thereof in proportions of 3 to 12 ml of solvent per gram of resin. To this is added BOC-L-proline in an amount of 1 to 6 equivalents per free amine equivalent of the BHA resin employed. After a period of mixing of 5 to 10 minutes, a coupling reagent (CA) such as dicyclohexyl carbodiimide (DCC) is added. Other diimide coupling agents may be used. The diimide coupling agent is used in the amount of 0.5 to 2.0 equivalents per equivalent of BOC-L-proline used.

The BOC-L-proline may be coupled in the absence of a coupling reagent if its active ester derivative, its azide derivative, its symetrical anhydride derivative, or a suitably chosen mixed anhydride derivative is used. The active ester derivatives that may be employed are 2-nitrophenyl ester, 4-nitrophenyl ester, pentafluorophenyl ester, N-hydroxysuccimide ester or equivalents thereof. The active esters are used in amounts of 1 to 10 equivalents per free amine equivalent of BHA resin.

The reaction mixture consisting of the BHA resin, the solvent, the BOC-L-proline, and the coupling reagent or BOC-L-proline active ester is stirred or shaken mechanically until the reaction is complete as is indicated by a ninhydrin test (E. Kaiser, et. al., Anal. Biochem., 34 595–8 [1970]) on a test sample. After completion of the coupling reaction, the BOC-L-proline resin may be washed with solvents such as methylene chloride, chloroform, methyl alcohol, benzene, dimethylformamide, or acetic acid. The amount of wash solvent may suitably be 2 to 20 ml of solvent for each gram of BHA resin used initially. If it is desired to terminate the coupling reaction before completion, the washing procedure is used and the remaining free amino groups on the BOC-L-proline resin may be blocked from further reaction by acetylation with an excess of acetylation reagents. The acetylation procedure is performed by agitating the BOC-L-proline resin with a solution of the acetylation reagent for a period of 0.5 to 12 hours. Acetylation reagents such as N-acetylimidazole in methylene chloride solution or a mixture of acetic anhydride and triethylamine in chloroform can be used. The acetylation reagent may be used in the amount of 0.5 to 5.0 equivalents per equivalent of free amine titer of the starting BHA resin.

The coupling reaction to produce the BOC-L-proline resin may be described by the following formula:

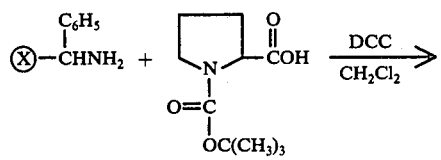

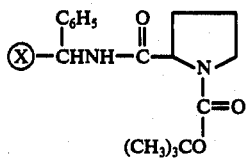

DEPROTECTION OF BOC-L-PROLINE RESIN

The BOC-L-proline resin produced as above described may be washed with a solvent such as referred to above and deprotected by agitating it with an agent such as a mixture of trifluoroacetic acid (TFA) in a solvent such as methylene chloride, chloroform, benzene or equivalents thereof. The amount of TFA in the solvent can vary from 10 to 100% of the mixture. The amount of TFA-solvent mixture may vary from 3 to 20 ml per gram of BHA resin used initially. The reaction time may be from about 10 minutes to 4 hours. The deprotection step is terminated by filtration to remove the TFA-solvent mixture. The residual TFA may be removed from the L-proline resin by washing with 3 to 20 ml per gram of BHA resin of a solution of 5 to 30% of triethylamine in a solvent such as methylene chloride, chloroform, benzene or equivalents thereof. Other tertiary or secondary organic amines may be used in place of the triethyl amine such as trimethylamine, N-ethyl piperidine, diisopropylamine or equivalents thereof. The free amine titer of the L-proline resin may be determined by the Dorman titration procedure (Dorman, L. C., Tetrahedron Letters, 1969 2319-21). The deprotection reaction may be described by the following formula:

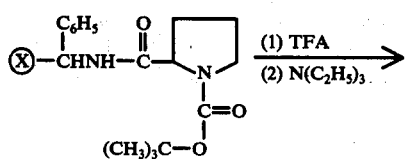

CYCLE 31

The prolyl BHA resin obtained as a result of cycle 32 may be suspended in a coupling solvent, the BOC-O-BZ-L-threonine derivative added and the mixture equilibrated in the same manner. The coupling agent, DCC, may be added and after completion of the reaction as indicated by the ninhydrin test, the reaction mixture is removed from the BOC-O-BZ-threonylprolyl BHA resin by filtration. The peptide resin may be washed with solvents. The amounts of reactants and solvents and reaction times may be the same as described in cycle 32. The BOC group may be removed from the peptide resin by the deprotection method described in the cycle 32. The resulting O-BZ-threonylprolyl BHA resin is then ready for cycle 30. The reactions of the cycle 31 may be shown by the following formula:

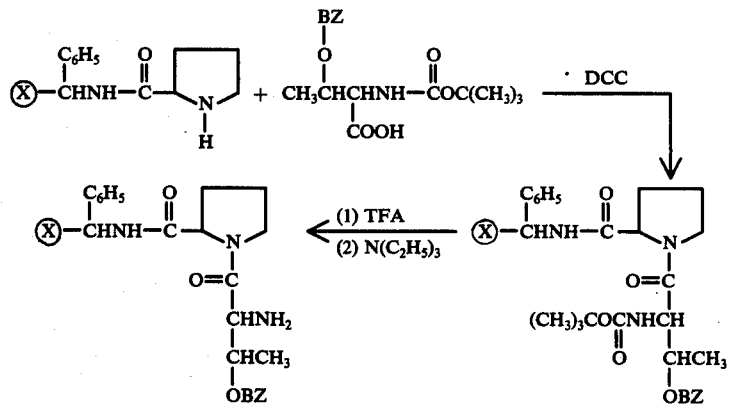

For convenience, we may write this resulting resin peptide using abbreviated nomenclature as follows:

CYCLE 30

In cycle 30 the coupling reaction and also the deprotection reaction may be performed in the same manner as in cycle 31 except that BOC-glycine is used in place of BOC-O-BZ-L-threonine. The reaction through coupling and deprotection may be written:

This compound, to our knowledge, has never been reported and as will later be shown may be converted to salmon calcitonin.

CYCLE 29

In cycle 29 the coupling and deprotection reactions may be performed in the same manner as in cycle 31 except for the substitution of BOC-O-BZ-L-serine as the amino acid derivative. This may be written:

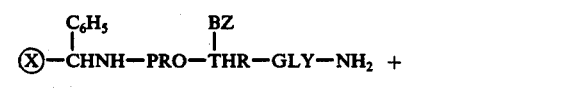

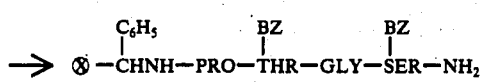

Cycle 28

In cycle 28 the coupling and deprotection reactions are performed as described in cycle 31 except the BOC-glycine is substituted as the amino acid reactant. These reactions through coupling and deprotection may be written as follows:

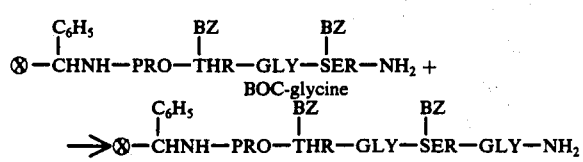

CYCLE 27

In this cycle the coupling and deprotection reactions may be as in cycle 31 using the same amino acid reactant, resulting in the following compound:

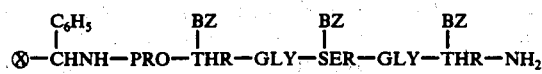

CYCLE 26

In cycle 26 the coupling reaction is performed using an active ester derivative of BOC-L-asparagine. The active ester procedure is used in place of the DCC coupling method to avoid a known side reaction that occurs with the use of DCC coupling agent with BOC-asparagine or BOC-glutamine. The reaction is performed using the active ester derivative of BOC-L-asparagine in the amount of 2 to 10 equivalents per free amine equivalent of BHA resin in dimethylformamide, mixtures of dimethylformamide with benzene, methylene chloride or chloroform or with equivalents thereof in amounts of 2 to 20 ml of solvent per gram of BHA resin used initially. Reaction times are from 1 to 72 hours. The reaction mixture is removed from the BOC-peptide resin by filtration after completion of the reaction as indicated by a ninhydrin test. The active esters derivative employed may be 2-nitrophenyl esters, 4-nitrophenyl esters, pentafluorophenyl, or equivalents thereof. We use AE to designate the active ester portion of the derivative. The coupling reaction may be written:

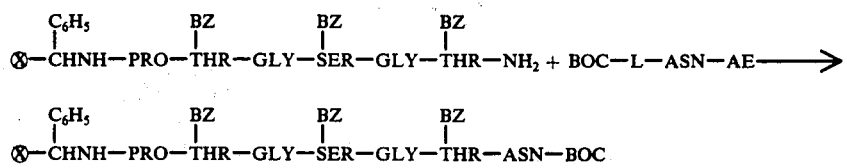

The deprotection reaction to remove the BOC group is performed as in cycle 32.

CYCLES 25 - 21

In each of cycles 25 to 21, the coupling and deprotection reactions may be conducted using the methods and proportions of reactants as in cycle 31 using BOC-BZ-L-theronine in cycle 25, BOC-ω-T-L-arginine in cycle 24, BOC-L-proline in cycle 23, BOC-W-L-tyrosine in cycle 22, and BOC-O-BZ-L-threonine in cycle 21. The compound resulting from the completion of cycle 21 may be written:

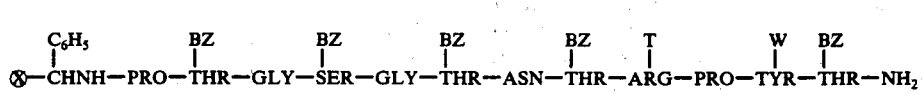

CYCLE 20

In cycle 20 the coupling and deprotection reactions may be performed using the methods and proportions of reactants as in cycle 26 using a BOC-L-glutamine active ester derivative as the amino acid derivative, resulting in the compound:

CYCLE 19

In cycle 19 the reactions are performed as in cycle 31 using BOC-L-leucine as the amino acid derivative. The compound resulting from cycle 19 is:

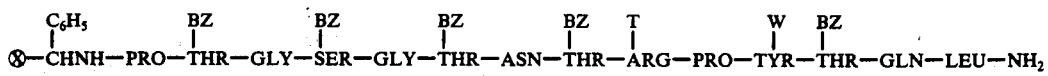

CYCLE 18

In cycle 18 we may use as the amino acid derivative BOC-ε-V-L-lysine. Otherwise, cycle 18 methods may be performed as in cycle 31 resulting in the compound:

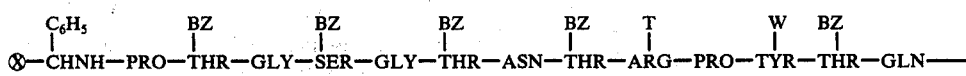

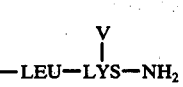

CYCLES 17 – 15

Cycles 17 to 15 may be performed as in cycle 31 except for the use of BOC-N-(im)-V-L-histidine in cycle 17, BOC-L-leucine as the reactant in cycle 16 and BOC-L-glutamic acid BZ ester (BZ represents the same groups as it represents for serine and threonine) as the reactant in cycle 15, resulting in the following compound from cycle 15:

CYCLE 7

Cycle 7 may be performed as in cycle 31 except for the use of BOC-S-R-L-cysteine or for the amino acid derivative. The compounds resulting from cycle 7 are described by the formula:

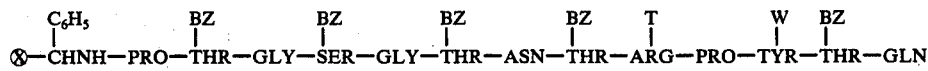

CYCLES 6 to 2

Cycles 6 to 4 were performed as in cycle 31 except that BOC-O-BZ-L-threonine was used as the amino acid derivative in cycle 6, BOC-BZ-L-serine was used as the amino acid derivative in cycle 5 and BOC-L-leucine was used in cycle 4 as the amino acid derivative. Cycle 3 may be performed identically to cycle 26 using BOC-L-asparagine active ester. In cycle 2 the procedures may be the same as cycle 31 using BOC-O-BZ-L-serine as the amino acid derivative. The compound resulting from cycle 2 is:

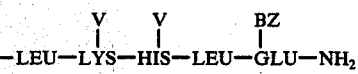

CYCLES 14 – 8

Cycle 14 may be performed identically to cycle 20 using BOC-L-glutamine-AE as the amino acid derivative. Cycles 13 to 8 may be performed as in cycle 31 except for the use of BOC-O-BZ-L-serine in cycle 13, BOC-L-leucine in cycle 12, BOC-ε-V-L-lysine in cycle 11, BOC-glycine in cycle 10, BOC-L-leucine in cycle 9, and BOC-L-valine in cycle 8 resulting in the compound:

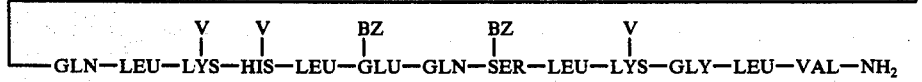

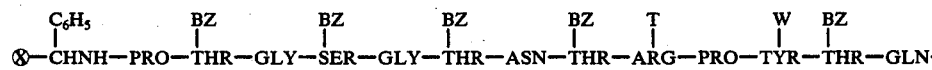

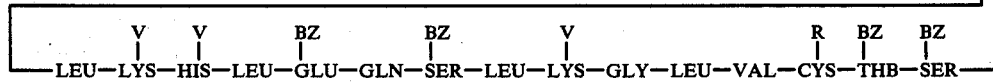

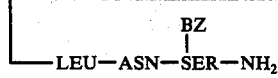

CYCLE 1

This cycle may be performed identically to cycle 7 using BOC-S-R-L-cysteine derivatives. The R group chosen for the cysteine may be the same as used in cycle 7 or different. For example, if the derivative chosen for the cycle 7 is BOC-S-ethylthio-L-cysteine the derivative in cycle 1 may be BOC-S-4-methoxybenzyl-L-cysteine or if BOC-S-4-methoxybenzyl-L-cysteine was chosen for cycle 7, then this derivative may be used also in cycle 1. The compounds resulting from cycle 1 are described by the formula:

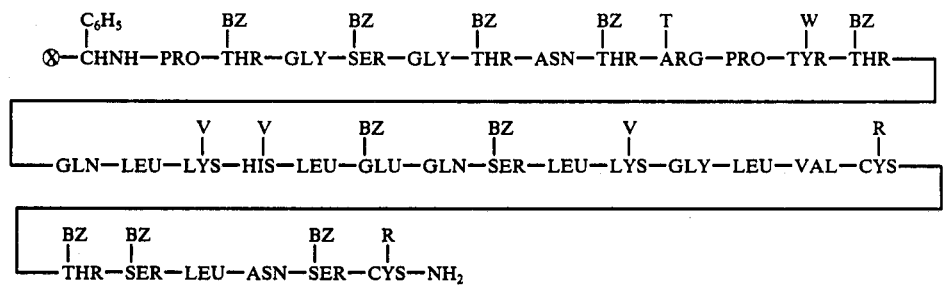

Cycle 1 represents the completion of the salmon calcitonin resin peptide. The resine peptide may be removed from the reaction vessel and dried in a vacuum. The weight of the resin peptide may be expected to be from 2.0 to 3.5 times the weight of BHA resin used initially in the synthesis.

RESIN PEPTIDE CLEAVAGE

The peptide is cleaved from the resin peptide resulting from cycle 1 by treatment with liquid hydrogen fluoride (HF). The HF cleavage reaction may be performed by treating a mixture of the resin peptide and anisole (0.5 to 5 ml for each gram of resin peptide) with liquid HF (2 to 20 ml for each gram of resin peptide) for 0.5 to 20 hours at −20° to °15° C. After the reaction period the excess HF may be removed by evaporation and the resulting mixture of peptide and resin beads may be extracted with an organic solvent such as ethyl acetate, diethyl ether, benzene or the like to remove the anisole and residual of HF. The peptide may be separated from the resin beads by extraction into aqueous acetic acid. The peptide at this stage is not cyclic salmon calcitonin but is the non-cyclic product without the cyclic disulfide bond between the cysteines at positions 1 to 7 in the molecule.

The HF treatment removes all blocking groups from the peptide except in the materials that were prepared using the S-alkylthio blocking groups on the thiol functions of cysteine residues at either positions 7 to 1. The S-n-alkylthio-L-cysteine residue is stable to the HF cleavage procedure and remains intact throughout the cleavage and extraction procedure. The S-BZ-L-cysteine residue is cleaved by HF to yield a cysteine residue with a free thiol function. Both types of blocking groups have been employed during our synthesis either singly or in combination with each other at positions 7 and 1. Thus, the peptides obtained after HF cleavage can be one of several types depending upon the blocking groups chosen for the thiol function of the cysteine derivative used during the resin peptide synthesis.

If BOC-S-BZ-L-cysteine derivatives were used in resin peptide synthesis cycles 7 and 1, the peptide resulting after HF cleavage would be of Type 1 and would have free thiol functions at both cysteine residues. The peptide would be represented by the formula:

TYPE I

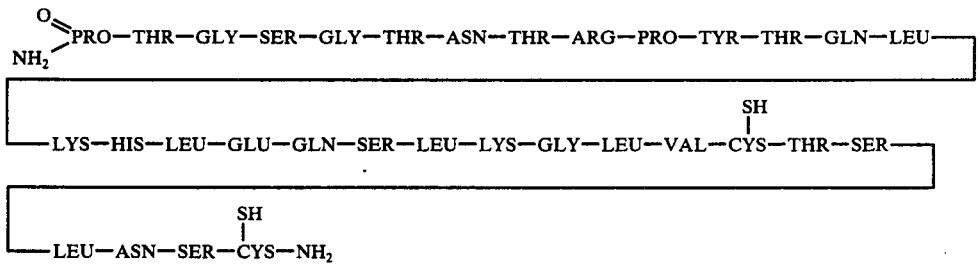

If BOC-S-n-alkylthio-L-cysteine derivatives were used in cycle 7 and the BOC-S-BZ-L-cysteines were used in position 1, the peptide resulting from the cleavage would be of the Type II and would be represented by the formula:

TYPE II

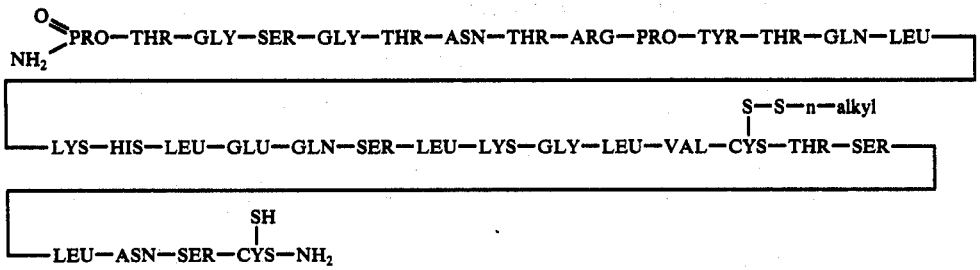

If BOC-S-BZ-L-cysteine was used at position 7 and BOC-S-n-alkylthio-L-cysteine was used at position 1, the peptide resulting from HF cleavage would be a Type III peptide and is represented by the formula:

TYPE III

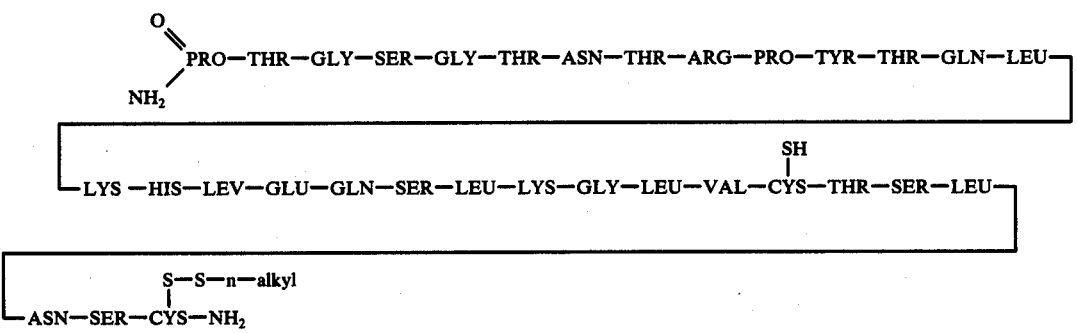

Each of the three types above described can be converted to fully active salmon calcitonin by methods we will describe as follows.

FORMATION OF DISULFIDE RING STRUCTURE

The crude peptide solution obtained from the HF cleavage procedure may be converted to active salmon clacitonin by converting the non-cyclic peptide to the cyclic form with a disulfide bond between the cysteine residues at positions 1 to 7. The procedure employed for the disulfide ring formation is determined by the cysteine derivatives used during the resin peptide synthesis. The Type I peptide obtained after HF cleavage of the resin peptide requires as oxidative ring formation procedure. With Type II and III peptides, a novel non-oxidative procedure may be employed. These methods are described below.

TYPE I PEPTIDE

Type I peptide contains cysteine residues with free thiol groups. The disulfide ring closure is performed by an oxidative procedure. The reaction can utilize atmospheric oxygen as the oxidizing agent. The crude aqueous acetic acid solution of the peptide obtained from the HF cleavage may be diluted with distilled water to a volume of 50 to 200 ml per gram of resin peptide cleaved. The pH of this solution may be raised from 6.0 to 8.5 by the addition of ammonium hydroxide solution. Air may be entrained into the solution for 2 to 20 hours or until no free thiol can be detected in the solution. The pH of the solution is lowered to 3 to 5 by addition of acetic acid. The peptide has now been converted to salmon calcitonin and can be purified. Other oxidizing agents may be used in place of atmospheric oxygen such as ferricyanide ion and diazene dicarboxylic acid (N,N-dimethyl amide). The reaction is illustrated below:

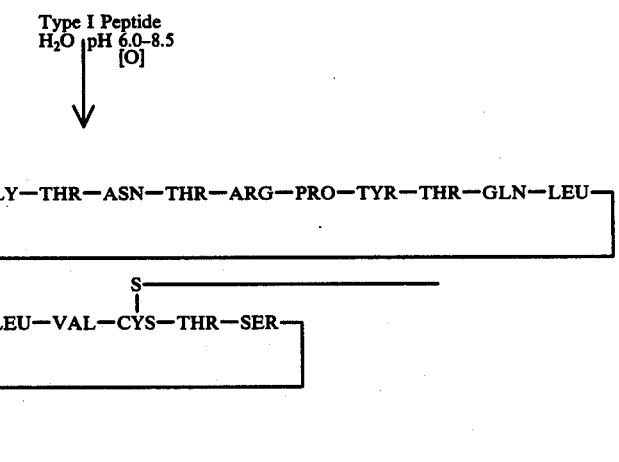

The peptide has now been converted to salmon calcitonin. The crude peptide solution obtained can be purified chromatographically to yield a freeze-dried product identical in chemical properties and biological activity to natural salmon calcitonin.

TYPE II PEPTIDE

The Type II peptide contains a free thiol at cysteine position 1 and a S-n-alkylthio group at cysteine position 7. This peptide is converted to cyclic salmon calcitonin by the novel non-oxidative procedure set forth in our copending application Ser. No. 505,344. This method involves the rearrangement of disulfide bonds to form the internal disulfide bond in salmon calcitonin with the displacement of n-alkylmercaptan. This reaction is represented as follows:

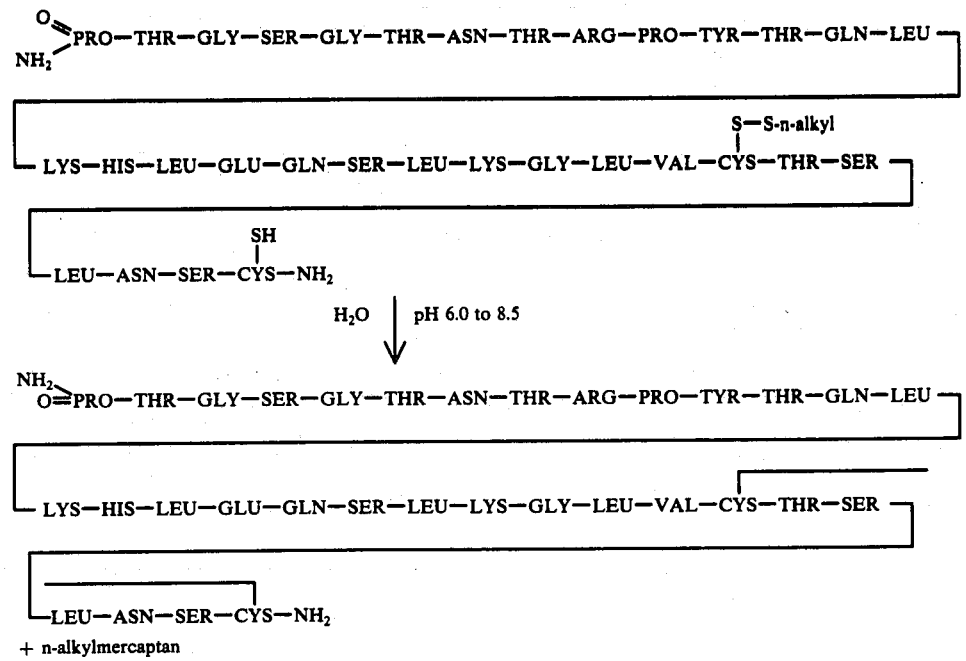

TYPE III PEPTIDE

The Type III peptide contains a free thiol at cysteine position No. 7 and a S-n-alkylthio group at cysteine position No. 1. This peptide also may be converted to cyclic salmon calcitonin by the novel non-oxidative procedure set forth in our copending application Ser. No. 505,344. which involves the rearrangement of disulfide bonds to form the internal disulfide bond in salmon calcitonin with the displacement of n-alkylmercaptan. This reaction is illustrated as follows:

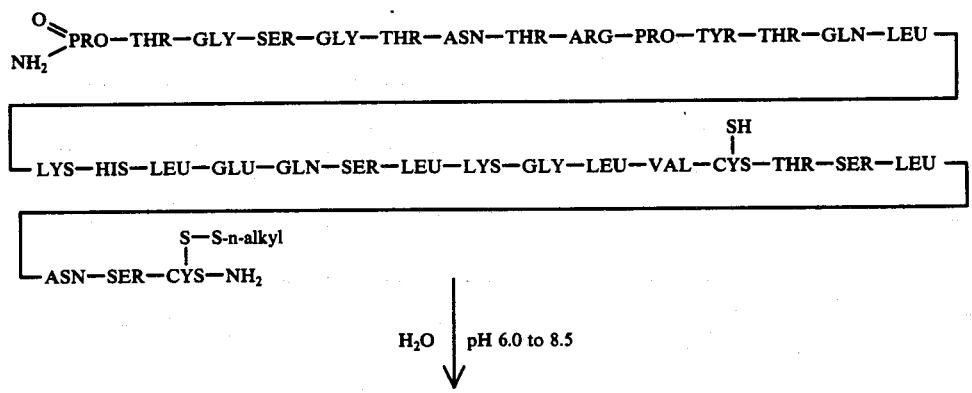

-continued

```
NH₂
  \
   O=PRO—THR—GLY—SER—GLY—THR—ASN—THR—ARG—PRO—TYR—THR—GLN—LEU ┐
                                                              │
   ┌──────────────────────────────────────────────────────────┘
   │                                        ┌─────────────────
   └─LYS—HIS—LEU—GLU—GLN—SER—LEU—LYS—GLY—LEU—VAL—CYS—THR—SER ┐
                                                              │
   ┌──────────────────────────────────────────────────────────┘
   │       ┌────────────────
   └─LEU—ASN—SER—CYS—NH₂
```

+ alkylmercaptan

The reaction may be performed with either Type II or Type III peptides by diluting with distilled water the aqueous acetic acid solution of the crude Type II or III peptide from HF cleavage to a final volume of 50 to 200 ml per gram of resin peptide cleaved. The pH of this solution is adjusted to 6 to 9 by the addition of ammonium hydroxide solution and the mixture is stirred in a closed container under a stream of an inert gas such as nitrogen for 2 to 48 hours. The reaction period can be stopped when the off-gas stream no longer contains n-alkylmercaptan. The pH of the reaction mixture may be lowered to 3.5 to 5.5 by the addition of glacial acetic acid.

The peptide has now been converted to salmon calcitonin. The crude peptide solution obtained can be purified chromatographically to yield a freeze-dried product identical in chemical properties and biological activity to natural salmon calcitonin.

PURIFICATION OF CRUDE SALMON CALCITONIN

The crude salmon calcitonin solutions at pH 5.0 from the above synthesis may be concentrated using an ion-exchange procedure. The concentrate may be purified by a combination of gel-filtration procedures and ion-exchange chromatography methods. The final purified product may be obtained from solution by freeze-drying as a fluffy white solid. This product will be found to be chemically and biologically equivalent to the product reported in literature (Guttman, S., et. al., Helv. Chim. Acta 52, 1789-95 [1969]). The product gives the correct amino acid analysis for salmon calcitonin.

Following are specific examples of the preparation of calcitonin in accordance with our procedures.

EXAMPLE 1

Resin Activation

The BHA resin (5 g) with an amine titer of 0.61 meq/g was placed in the reactor vessel of a peptide synthesizer marketed by Schwarz-Mann, Inc. of Orangeburg, New York. The resin was treated with 25 ml of the following solvents filtering after each treatment.

Methylene chloride for 2 minutes
Chloroform for 2 minutes two times each
10% triethylamine in chloroform for 5 minutes two times each
Chloroform for 2 minutes
Methylene chloride for 2 minutes three times each

CYCLE 32

Coupling: The BHA resin, 25 ml of methylene chloride and 1.29 g (0.006 moles) of BOC-L-proline was stirred for 10 minutes. 6.0 ml of a methylene chloride solution of dicyclohexylcarbodiimide (1 milliequivalent of DCCI per 1 ml of solution) was added to the reactor and the mixture agitated for 6 hours. The reaction mixture was removed from the reactor by filtration and the BOC-prolyl BHA resin subjected to the following successive 2 minute, 25 ml washes, removing the wash by filtration each time:
Methylene chloride two times
Methyl alcohol two times
Methylene chloride three times Acetylation: The resin was then agitated with a mixture of 1.5 ml of triethylamine (TEA), 1 ml of acetic anhydride and 25 ml of chloroform for 2 hours. The reaction mixture was removed by filtration and the resin subjected to the following 2 minute, 25 ml washes:
Chloroform two times
Methyl alcohol two times
Methylene chloride three times.

Deprotection: The BOC-protected resin was agitated for 5 minutes with a mixture of 15 ml of the trifluoroacetic acid (TFA) and 15 ml of methylene chloride. This mixture was removed by filtration and the resin was agitated with a second mixture of 15 ml of TFA and 15 ml of methylene chloride for 30 minutes. The reaction mixture was removed by filtration and the resin subjected to the following 25 ml washes:
Methylene chloride two times 2 minutes each
Methylenealcohol two times 2 minutes each
Chloroform two times 2 minutes each
10% TEA in chloroform two times 10 minutes each
Chloroform two times two minutes each
Methylene chloride two times two minutes each The L-proline BHA resin was titrated to establish the amine or proline titer. This value was 0.55 milliequivalents of amine or proline per gram of resin.

CYCLE 31

Coupling: The L-prolyl resin, 25 ml of methylene chloride and 1.7 g (0.0055 mole) of BOC-O-benzyl-L-threonine were agitated for 10 minutes. Then 5.5 ml of a methylene chloride solution of dicyclohexylcarbodiimide (1 milliequivalent of DCCI per 1 ml of solution or a total of 0.0055 mole of DCCI) was added to the reactor and the mixture agitated for 2 hours. The reaction mixture was removed from the reactor and the resin was subjected to the following successive 2 minute, 25 ml washes, removing the wash by filtration each time.
Methylene chloride two times
Methyl alcohol two times
Methylene chloride three times;
A ninhydrin test was negative.
Deprotection: The deprotection procedure described in Cycle 32 was repeated for this cycle.

CYCLE 30 through 27

The coupling and deprotection procedures used in these cycles were the same as in Cycle 31 except that the following amino acid derivatives were used in place of the threonine derivative:
Cycle 30 — 0.97 g (0.0055 mole) of BOC-glycine
Cycle 29 — 1.62 g (0.0055 mole) of BOC-O-Benzyl-L-serine
Cycle 28 — The material used was the same as Cycle 30.
Cycle 27 — The material used was the same as Cycle 31.

CYCLE 26

Coupling: The peptide resin obtained from Cycle 27 was washed twice with 25 ml portions of dimethylformamide (DMF). The resin was then agitated for 24 hours with a solution of 2.9 g (0.008 mole) of BOC-L-asparagine p-nitro-phenyl ester in 35 ml of DMF. The reaction mixture was filtered and the resin peptide subjected to two minute washes with two successive 25 ml portions of the following solvents: DMF, methylene chloride, methanol, methylene chloride. Each individual solvent was removed by filtration. A ninhydrin test was negative.
Deprotection: The deprotection procedure used in Cycle 32 was repeated.

CYCLE 25

Coupling and deprotection procedures were the same as in Cycle 31 using the same materials and amounts.

CYCLE 24

Coupling: The resin peptide obtained from Cycle 25 was washed with two successive 25 ml portions of DMF. The resin peptide was then agitated for 10 minutes with a mixture of 3.43 g (0.008 mole) of BOC-N-γ-tosyl-L-arginine and 25 ml of DMF. Then 8 ml of DCCI in methylene chloride(equivalent to 0.008 mole of DCCI) was added and the mixture agitated for 6 hours. The reaction mixture was removed by filtration. The resin peptide was subjected to two minutes washes with two successive 25 ml portions of the following solvents: DMF, methylene chloride, methyl alcohol, methylene chloride. The ninhydrin test was negative.
Deprotection: Repeat deprotection procedures used in Cycle 32.

CYCLE 23

Coupling: The peptide resin obtained from Cycle 24 was agitated for 10 minutes with 1.77 g (0.008 mole) of BOC-L-proline and 25 ml of methylene chloride. 8 ml of DCCI in methylene chloride (equivalent to 0.008 mole of DCCI) was added and the mixture agitated for 6 hours. The reaction mixture was removed by filtration and the resin peptide subjected to two minute washes with two successive 25 ml portions of the following solvents: methylene chloride, methyl alcohol, methylene chloride, Each individual wash was removed by filtration. The ninhydrin test was negative.
Deprotection: The deprotection procedure used in Cycle 32 was repeated.

CYCLES 22 and 21

The coupling and deprotection procedures used in these cycles were the same as in Cycle 24 except that in the coupling reaction the following amino acid derivatives were used in place of BOC-L-proline.
Cycle 22 — 2.97 g (0.008 mole) of BOC-O-benzyl-L-tyrosine
Cycle 21 — 2.47 g (0.008 mole) of BOC-O-benzyl-L-threonine.

CYCLE 20

This procedure is the same as Cycle 26 except that 23.0 g (0.008 mole) of BOC-L-glutamine p-nitrophenyl ester is used in place of the asparagine derivative.

CYCLES 19 through 15

The procedure is the same as used in Cycle 31 except that the following amino acid derivatives were used in place of the threonine derivative:
Cycle 19 — 1.37 g (0.0055 mole) of BOC-L-leucine
Cycle 18 — 2.09 g (0.0055 mole) of BOC-ε-carbobenzyloxy-L-lysine
Cycle 17 — 2.58 g (0.0055 mole) of BOC-N(im)-carbobenzyloxy-L-histidine
Cycle 16 — See Cycle 19
Cycle 15 — 1.85 g (0.0055 mole) of BOC-L-glutamic acid γ-benzyl ester.

CYCLE 14

Same as cycle 20

CYCLE 13

The procedure used was the same as used in Cycle 23 except that in the coupling reaction 2.36g (0.008 mole) of BOC-O-benzyl-L-serine was used in place of the proline derivative.

CYCLE 12 through 9

The procedures used were the same as used in Cycle 31 except in the coupling reactions the following amino acid derivatives were used in place of the threonine derivative.
Cycle 12 — Same material as used in Cycle 19
Cycle 11 — The material used was the same as in Cycle 18
Cycle 10 — Same material as used in Cycle 30
Cycle 9 — Same material as used in Cycle 19.

CYCLE 8

Coupling: The resin peptide from Cycle 9 was agitated for 10 minutes with 1.79g (0.008 mole) of BOC-L- valine and 25 ml of methylene chloride. Then 8 ml of DCCI in methylene chloride (equivalent to 0.008 mole of DCCI) was added and the mixture agitated for 16 hours. The reaction mixture was removed by filtration. The resin peptide was subjected to two minutes washes with two successive 25 ml portions of the following solvents: methylene chloride, methyl alcohol, methylene chloride. Each individual wash was removed by filtration.

Deprotection: See Cycle 32.

CYCLE 7

The procedure was the same as used in Cycle 31 except that in the coupling reaction 1.55g (0.0055 mole) of BOC-S-ethylthio-L-cysteine was used in place of the threonine derivative.

CYCLE 6

The materials and procedures used were the same as Cycle 31.

CYCLE 5

The materials and procedures used were the same as Cycle 29.

CYCLE 4

The materials and procedures used were the same as Cycle 19.

CYCLE 3

The materials and procedures used were the same as Cycle 26.

CYCLE 2

The materials and procedures used were the same as Cycle 29.

CYCLE 1

The procedures used were the same as used in Cycle 31 except that 1.88g (0.0055 mole) of BOC-S-p-methoxybenzyl-L-cysteine was used in place of the threonine derivative.

After completion of Cycle 1 the resin peptide was washed with two successive 25 ml portions of n-hexane. The peptide material was removed from the reactor and dried in an electric vacuum oven at 40° C and 0.1 mm of Hg for 24 hours.

CLEAVAGE WITH HYDROGEN FLUORIDE

The dried resin peptide (16 g) and 16 ml of anisole were placed in a teflon reaction vessel. The vessel equipped with a teflon-coated magnetic stirrer was placed in a dry ice-acetone bath and 100 ml of hydrogen fluoride gas was condensed into the vessel. This mixture was stirred at 0° C. in an ice bath for 1 hour. The hydrogen fluoride was removed by evaporation at reduced pressure. The residue was triturated with six 100 ml portions of ethyl acetate. The peptide was extracted from the resin beads with 800 ml of 0.1 molar aqueous acetic solution.

CYCLIZATION OF PEPTIDE TO SALMON CALCITONIN

The aqueous acetic acid extract obtained from hydrogen fluoride cleavage was diluted to 1.5 liters by addition 700 ml of distilled water. The pH of the solution was adjusted to 7.5 by the addition of concentrated ammonium hydroxide. The solution was stirred in a closed vessel under a stream of nitrogen for 24 hours. At this time no ethyl mercaptan could be detected in the emerging nitrogen stream. The ethyl mercaptan content of the nitrogen stream was measured by passing the stream through a solution of Ellman's reagent (Ellman, G. L., Arch. Biochem. Biophys., 82 70-7 (1959). The pH of the reaction mixture was adjusted to 0.5 by addition of glacial acetic acid.

PURIFICATION OF THE CRUDE SALMON CALCITONIN

The 1.5 liters of solution from the above synthesis at pH 5.0 was concentrated using a SP-Sephadex C-25 ion-exchange column. The 75 ml concentrate removed from the column with 0.5 molar sodium chloride solution was desalted and purified by passing through a Sephadex G-25 (fine) gel-filtration column and eluting with 0.30 molar aqueous acetic acid solution. The salmon calcitonin fraction from this column was adjusted to pH 6.0 by addition of ammonium hydroxide solution. This solution was further purified by ion-exchange chromatography using a Whatman CM52 column eluted with ammonium acetate buffer. The salmon calcitonin fraction from this column was adjusted to pH 5.0 by addition of glacial acetic acid. This solution was concentrated using a SP-Sephadex C-25 ion-exchange column. The 30 ml concentrate removed from the column with 0.5 molar sodium chloride solution was desalted with a Sephadex G-25 (fine) gel-filtration column. The purified salmon calcitonin fraction was collected and freeze-dried. The product was obtained as a fluffy white solid. This material was found to be biologically and chemically equivalent to the product reported in literature (Guttmann, S., et. al., Helv. Chim. Acta 52, 1789-1795 [1969]).

The preparation of the compounds as heretofore described or as set forth in Example 1 may be varied in many respects, but when variations in more than one factor are made it is difficult to evaluate any one of the changed factors. For this reason we set up a series of tests in which only one factor is varied and the results compared.

EXAMPLE 2

The procedures set forth in Example 1 were repeated using the same materials and the same amounts with all conditions maintained identical insofar as this was practically possible, except that in cycle 24 BOC-ω-tosyl-L-arginine was replaced with 2.55 grams (0.008 mole) of BOC-ω-nitro-arginine. The results obtained were substantially identical to that reported in Example 1.

EXAMPLE 3

The process set forth in Example 1 were repeated using the same materials, the same amounts, and the same conditions, except that in cycle 22 the BOC-O-benzl-L-tyrosine was replaced with 3.45 g (0.008 mole) of BOC-O-2-bromobenzyoxycarbonyl-L-tyrosine. Results obtained were similar to that reported in Example 1.

EXAMPLE 4

All procedures, materials, and conditions were maintained the same as in Example 1 except that in cycles 18 and 11 the BOC-ε-benzyloxycarbonyl-L-lysine was replaced at each of these cycles with 2.28 g (0.0055 mole) of BOC-ε-2-chlorobenzyloxycarbonyl-L-lysine.

Results were obtained substantially the same as in Example 1.

EXAMPLE 5

The materials, procedures, and conditions for the resin peptide synthesis may be used as in Example 1 except that in cycle 7 the BOC-S-ethylthio-L-cysteine was replaced with 1.88 g (0.0055 mole) of BOC-S-$p$-methoxybenzyl-L-cysteine thus to prepare the Type I peptide.

The aqueous acetic acid extract obtained from the hydrofluoride cleavage may be diluted to 1.5 liters by addition by 800 ml of distilled water and the pH adjusted to 7.0 by the addition of concentrated ammonium hydroxide. A stream of air then may be entrained into the solution for a period of 8 hours. The pH of the reaction mixture may then be lowered to 5.0 by the addition of glacial acetic acid. Purification of the crude salmon calcitonin can be done in accordance with the same procedure as described in Example I.

EXAMPLE 6

All materials, procedures and conditions may be held to those of Example 1 except that in cycle 7 the BOC-S-ethylthio-L-cysteine by replaced with 1.48 g (0.0055 mole) of BOC-S-methylthio-L-cysteine.

Results may be expected similar to those obtained in Example 1.

EXAMPLE 7

All materials, procedures, and conditions may be held to those of Example 1 except that in cycle 1 the BOC-S-p-methoxybenzyl-L-cysteine be replaced by 1.66 g (0.0055 mole) of BOC-S-3,4-dimethylbenzyl-L-cysteine. We may except results similar to those set forth in Example 1.

EXAMPLE 8

All materials, procedures, and conditions may be held to those for Example 1 except for the following changes:

| Cycle | Change |
|---|---|
| 1 | Use 1.71 g (0.0055 mole) of BOC-S-benzyl-L-cysteine in place of BOC-S-p-methoxybenzyl-L-cysteine. |
| 7 | Use 1.48 g (0.0055 mole) of BOC-S-methylthio-L-cysteine in place of BOC-S-ethylthio-L-cysteine. |
| 11 | Use 2.28 g (0.0055 mole) of BOC-$\epsilon$-2-chlorobenzyl-oxycarbonyl-L-lysine in place of BOC-$\epsilon$-benzyl-oxycarbonyl-L-lysine |
| 18 | Same as Cycle 11 above |
| 22 | Use 3.95 g (0.008 mole) of BOC-O-2-bromobenzyl-oxycarbonyl-L-tyrosine in place of BOC-O-benzyl-L-tyrosine |
| 24 | Use 2.55 g (0.008 mole) of BOC-$\Omega$-nitro-L-arginine in place of BOC-N-$\gamma$-tosyl-arginine |

Results similar to those of Example 1 would be expected.

EXAMPLE 9

All materials, procedures and conditions may be held in those of Example 1, except that in cycle 7 the amino acid derivative may be 1.88 g (0.0055 mole) of BOC-S-p-methoxybenzyl-L-cysteine and in cycle 1 the amino acid derivative may be 1.55 g (0.0055 mole) of BOC-S-ethylthio-L-cysteine, thus to prepare the Type III peptide.

Cyclization of the Type III peptide and purification of the cyclized product should yield salmon calcitonin as in Example 1.

While only certain embodiments of our invention have been described in specific detail it will be apparent to those skilled in this art that other specific embodiments may be practiced, and many changes may be made all within the spirit of the invention, and it is intended that all such other embodiments and changes be considered within the scope of the appended claims.

We claim:

1. A resin peptide having the structure:

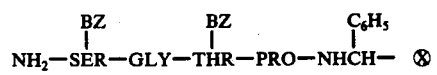

where $\widehat{X}$ is divinylbenzene crosslinked polystyrene resin and BZ is benzyl, 4-methoxybenzyl, 3-4 dimethylbenzyl, 4-chlorobenzyl, 2-6 dichlorobenzyl, 4-nitrobenzyl, or benzhydryl.

2. A resin peptide having the structure:

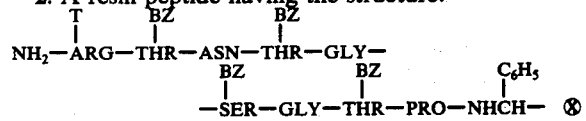

where $\widehat{X}$ is divinylbenzene crosslinked polystyrene resin BZ is benzyl, 4-methylbenzyl, 3-4 dimethylbenzyl, 4-chlorobenzyl, 2-6 dichlorobenzyl, 4-nitrobenzyl, or benzhydryl, and T is nitro or tosyl.

* * * * *